United States Patent [19]

Wiegman

[11] Patent Number: 4,592,018

[45] Date of Patent: May 27, 1986

[54] REMOVABLE RAM PACKAGE FOR AMBULATORY MEDICAL MONITOR

[75] Inventor: Douglas C. Wiegman, Bellevue, Wash.

[73] Assignee: Vita-Stat Medical Services, Inc., Bellevue, Wash.

[21] Appl. No.: 527,453

[22] Filed: Aug. 29, 1983

[51] Int. Cl.[4] .................... G11C 5/06; G11C 17/00
[52] U.S. Cl. ............................ 365/63; 365/226; 365/195; 323/911; 307/328
[58] Field of Search .............. 365/63, 72, 52, 226, 365/229, 195; 324/51; 339/113 R; 307/328; 340/653; 323/911

[56] References Cited

U.S. PATENT DOCUMENTS

| | | |
|---|---|---|
| 3,898,631 | 8/1975 | Brown et al. .................... 365/52 |
| 4,042,832 | 8/1977 | Cassarino, Jr. et al. ......... 340/653 |
| 4,502,130 | 2/1985 | Kuckuk ........................... 365/72 |

FOREIGN PATENT DOCUMENTS

| | | |
|---|---|---|
| 0118078 | 7/1983 | Japan ............................. 365/226 |
| 2028555 | 3/1980 | United Kingdom ............. 365/52 |

OTHER PUBLICATIONS

Davis, "Solid State Cartridge System", IBM Technical Disclosure Bulletin, vol. 23, No. 5, Oct. 1980, pp. 1748–1750.

Primary Examiner—James W. Moffitt
Assistant Examiner—Glenn A. Gossage
Attorney, Agent, or Firm—Lawrence S. Levinson; Robert E. Lee, Jr.

[57] ABSTRACT

A removable package for use primarily in an ambulatory monitoring device, such as a medical monitor includes a RAM and a power supply. The RAM package is connected to an external device via an edge connector which includes interlock means for sensing when the removable RAM package is properly connected to the external device in order to prevent inadvertent writes into the RAM. In a preferred embodiment of the invention disclosed, the removable RAM circuit also includes a microprocessor compatible real time timer which is connected to the same data and address buses as the RAM.

10 Claims, 4 Drawing Figures

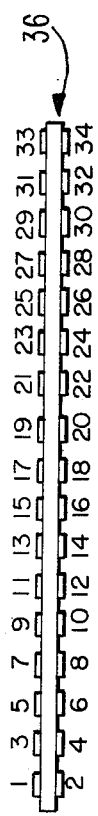
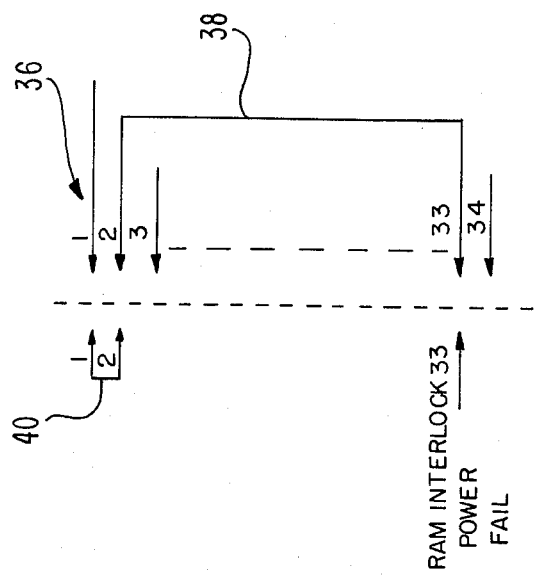
Fig. 2
Fig. 3

4,592,018

REMOVABLE RAM PACKAGE FOR AMBULATORY MEDICAL MONITOR

BACKGROUND OF THE INVENTION

The present invention relates to a removable RAM package for a data acquisition system. In particular, the present invention has utility in an ambulatory medical monitor such as an ambulatory blood pressure monitoring system.

A number of portable monitoring devices are used in medical monitoring. One well known device is the so-called Holter monitor which is an EKG monitor which typically uses a magnetic tape recorder to record EKG signals from a patient over extended periods of time. A patient whose EKG is being monitored usually wears a Holter monitor for 24 hours, during which time the monitor records EKG signals for later analysis by a physician.

Heretofore, very few portable monitoring devices existed for obtaining blood pressure readings over extended periods of time. The reason for this was twofold. First of all, there are very few automatic, non-invasive blood pressure monitoring devices in use today. Second, an improved recording means for collecting data in a portable blood pressure monitoring unit did not exist.

One known non-invasive blood pressure monitoring unit is the blood pressure cuff designed and sold by VitaStat Medical Services, Inc. and described more fully in U.S. Pat. No. 4,206,765 entitled CUFF MECHANISM which issued to T. G. Huber on June 10, 1980. This particular unit requires an air pump to pump up the cuff each time a reading is taken. Accordingly, an ambulatory blood pressure monitoring device must include means for energizing the air pump. While a battery would be suitable to provide electric power to the air pump, so much power is required to operate the air pump that some means of preserving battery power would also be desirable.

SUMMARY OF THE INVENTION

The present invention is a removable package containing a random access memory (RAM), a real time timer, and means for energizing the RAM when the package is properly plugged into either an ambulatory blood pressure monitoring device or into a computer readout device. The circuitry contained within the removable RAM package is able to determine if it is properly inserted into either the ambulatory blood pressure monitoring device or into the computer readout device before it energizes the RAM. The circuitry in the removable RAM package thereby prevents spurious signals on the input terminals of the package from destroying data contained within the removable RAM package.

BRIEF DESCRIPTION OF THE DRAWING

In the Drawing:

FIG. 2 illustrates the edge connector of the removable RAM package of the present invention; and FIG. 3 is a schematic diagram showing the manner in which the power interlock of the present invention operates.

DETAILED DESCRIPTION OF THE PREFERRED EMBODIMENT

Figure 1A:
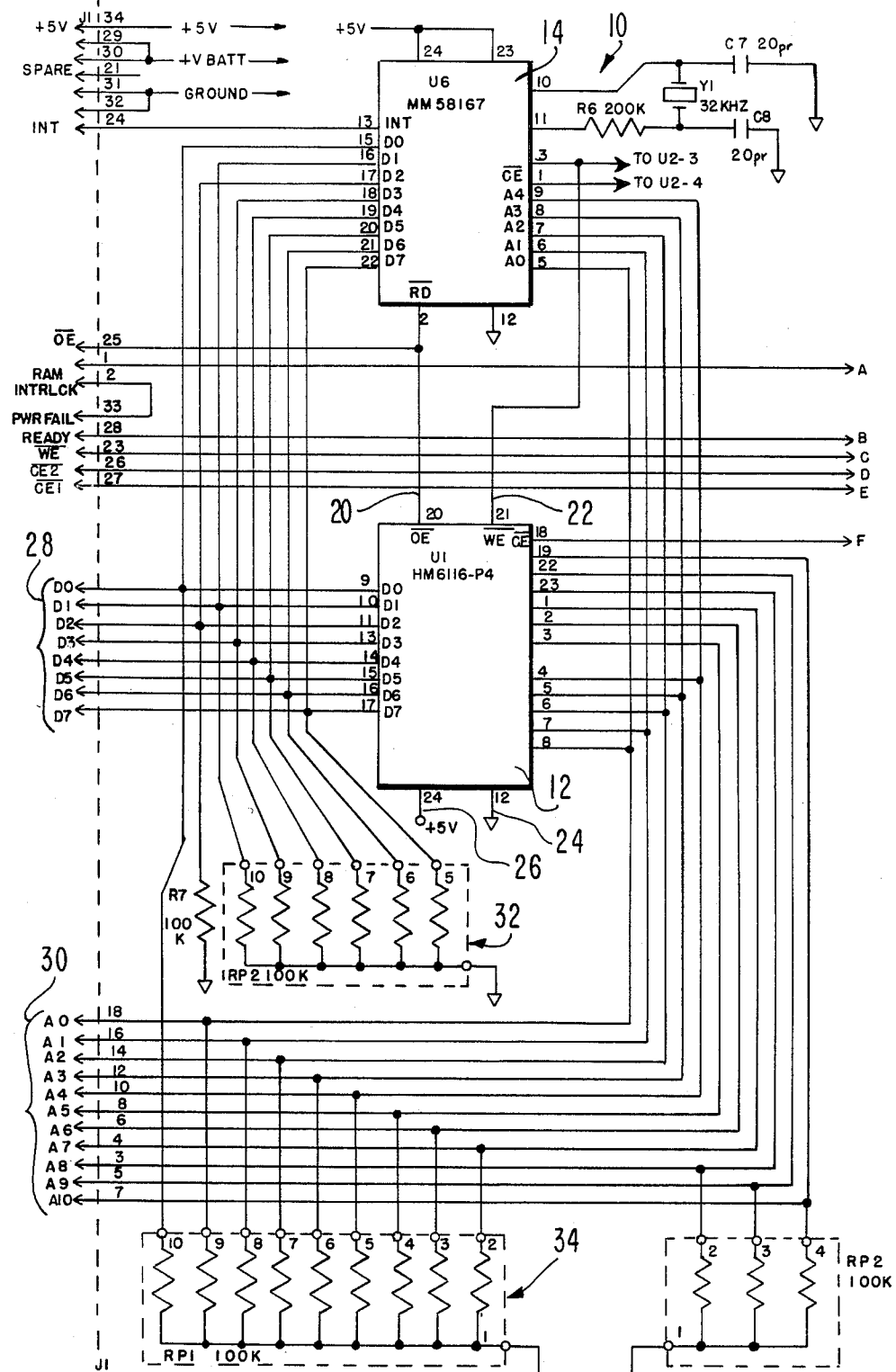
FIGS. 1a and 1b illustrate the circuitry of the removable RAM package of the present invention.
Figure 1B:
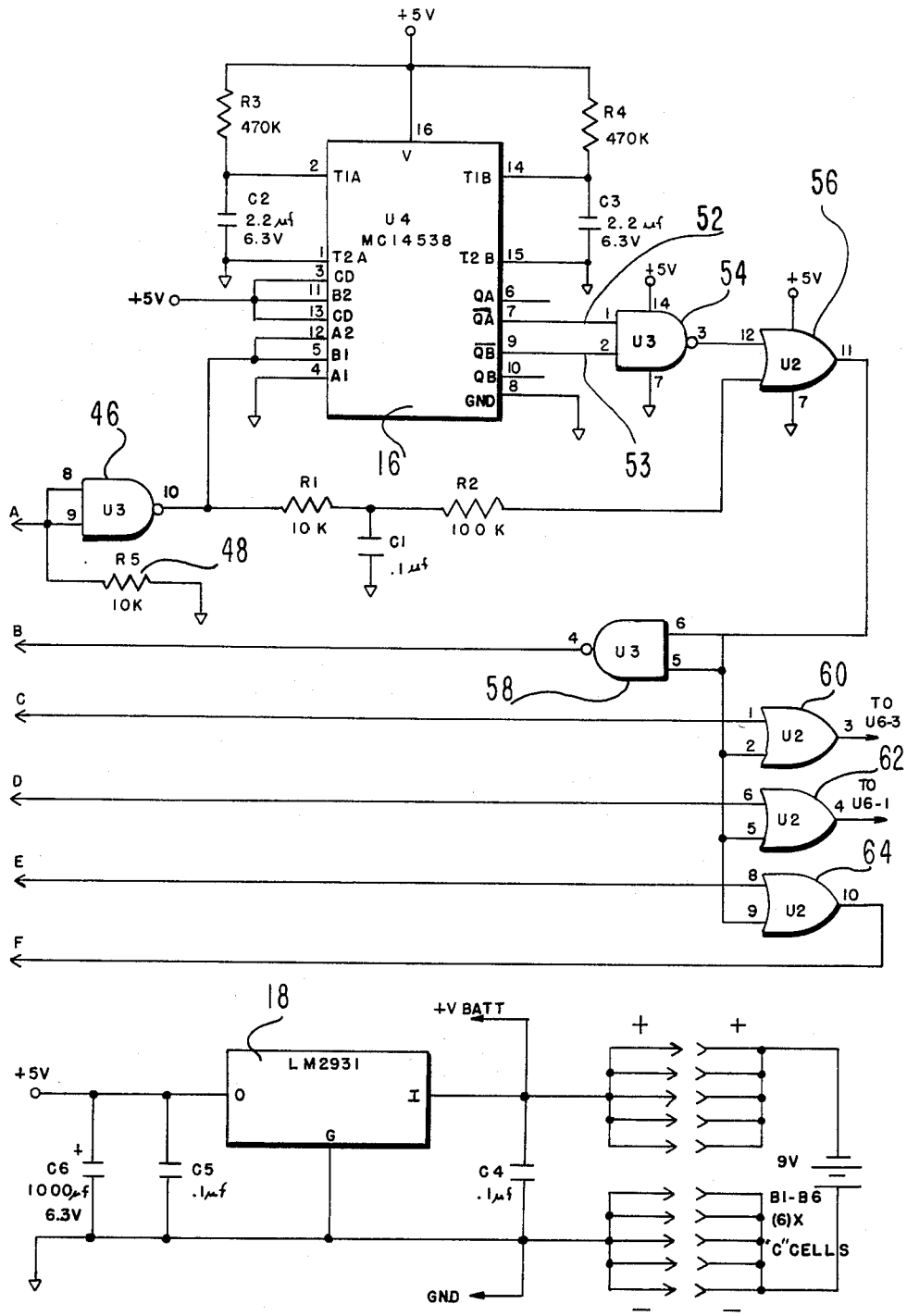

Referring generally to FIG. 1, the removable RAM package 10 of the present invention is comprised of RAM 12, a real time timer circuit 14, a dual one shot monostable multivibrator 16, and a voltage regulator 18. In the preferred embodiment of the invention the RAM 12 is a 2K×8 CMOS static RAM such as an HM6116, and the real time timer circuit 14 is a National Semiconductor MM58167 Microprocessor Compatible Real Time Clock Circuit.

The RAM 12 has a series of data lines D0–D7 and address lines A0–A10, an output enable line 20, a write enable line 22, and ground and positive power supply connections 24, 26, respectively. The real time timer 14 also has a series of data lines D0–D7, which are connected to the data lines D0–D7 of the RAM 12 on a common data bus 28. The real time timer circuit 14 is also connected to address lines A0–A4 on an address bus 30 which is also connected to the RAM 12. Each of the lines of the data bus 28 and each of the lines of the address bus 30 are connected to ground via a series of 100K resistors 32, 34, respectively.

It is very important, for the proper operation of the removable RAM package 10, for the circuitry to be able to know when the removable RAM package 10 is properly plugged into either an ambulatory monitoring device or into the computer readout device, either of which may hereinafter be referred to as an "external device". In order to prevent data stored in the RAM 12 or timing parameters stored in the real time timer 14 from being changed, a mechanism, comprising a combination of elements, is provided for assuring that the removable RAM package 10 is properly connected to an appropriate external device.

Referring now also to FIG. 2, an end view of the edge connector 36 which is used to connect the removable RAM package 10 to an external device is shown. The contacts on the edge connector 36 are numbered from 1 through 34, as shown, with the odd numbered contacts being on the top of the edge connector 36 and the even numbered contacts being on the bottom of the edge connector 36. With reference now to FIG. 3, contact number 2 and contact number 33 are connected together in the removable RAM package 10 via a jumper 38. Similarly, contact number 1 and contact number 2 are connected together via a jumper 40 in the external device (represented by the left side of the vertical dashed line). Accordingly, only when the edge connector 36 is fully inserted into the external device will full contact be made all along the edge connector 36, as represented by the contacts numbered 1 and 2 at one edge of the connector and the contacts number 33 at the distant edge of the connector 36, making full electrical contact. Accordingly, only then will line number 1 on the edge connector 36 of the removable RAM package 10 be connected to a RAM INTERLOCK POWER FAIL line (line number 33 on edge connector 36) in the external device.

With reference again to FIG. 1, once the edge connector 36 is fully plugged into the external device, the positive power supply voltage of the external device (on the RAM INTERLOCK POWER FAIL line 33 of the edge connector 36) will be present on line 1 of edge connector 36. The RAM INTERLOCK POWER FAIL line is the input to an inverter circuit 46. Normally, the input to inverter circuit 46 is kept low by a 10K pull-down resistor 48 when the removable RAM package 10 is not connected to an external device. When the removable RAM package 10 is properly connected to an external device, the output of the inverter 46 goes low. The negative going signal at the input of the dual one shot 16, a Motorola MC14538 integrated circuit in the preferred embodiment of the invention, causes line 52 to NAND gate 54 to go low for approximately 1.25 seconds (based upon the values of R3, R4, C2, and C3). That causes the output of NAND gate 54 to go high for approximately 1.25 seconds, causing the output of OR gate 56 to go high. The high output on OR gate 56 brings the output of NAND gate 58, corresponding to the READY signal on line 28 of edge connector 36, low.

The high output signal from OR gate 56 also causes the outputs of OR gates 60, 62, and 64 to go high. High outputs from gates 60, 62, and 64 disable the RAM and timer chips 12, 14. Both the RAM and timer chips 12, 14 remain disabled until there are no more transitions on the RAM INTERLOCK POWER FAIL line for more than 1.25 seconds. Any additional upward transitions on the RAM INTERLOCK POWER FAIL line will keep the RAM and timer chips 12, 14 disabled for the reasons set forth above. Similarly, any additional downward transitions on the RAM INTERLOCK POWER FAIL line will keep the RAM and timer chips 12, 14 disabled for 1.25 seconds, as the input line 53 to NAND gate 54 will be forced low. Accordingly, the signal on the RAM INTERLOCK POWER FAIL line must be stable in a high state for more than 1.25 seconds to allow the one shot 16 to stop timing out and to cause its pin 7 to go high thereby causing the output of NAND gate 54 and OR gate 56 to go low and stay low. This also causes the output of NAND gate 58 to go high, i.e. placing a high signal on the READY line, indicating to the external device that the removable RAM package 10 is ready for data acquisition. The same signal also allows writes to the RAM and timer chips 12, 14 since the outputs of OR gates 60, 62, and 64 will be controlled by the Write Enable and Chip Enable signals on edge connector 36 lines 23, 26, and 27, respectively, since the RAM INTERLOCK POWER FAIL controlled inputs of OR gates 60, 62, and 64 will be low, so the outputs of OR gates 60, 62, and 64 will be controlled exclusively by the inputs from the external device on lines 23, 26, and 27 of the edge connector 36.

I claim:
1. A removable RAM package for data acquisition comprising:
   (a) a power supply;
   (b) a RAM coupled to a data bus and an address bus, said RAM also electrically coupled to an elongated multiterminal edge connector for connecting the removable RAM package to an external device having an elongated multiterminal edge connector for mating engagement with said RAM package connector, said RAM being powered by said power supply;
   (c) an interlock circuit which senses when the removable RAM package is properly connected to said external device substantially along the entire length of said edge connectors, said interlock circuit being powered by said power supply, and said interlock circuit preventing writes to said RAM unless said removable RAM package is properly connected to said external device substantialy along the entire length of said edge connectors.

2. The removable RAM package of claim 1 wherein said interlock circuit comprises: means for sensing the level of a voltage on an interlock line in said external device; and means for preventing writes to said RAM until said sensed external voltage level from said external device has been stable in a predetermined state for a predetermined time period.

3. The removable RAM package of claim 2 wherein said sensed voltage level from said external device is derived from said power supply voltage of said RAM package.

4. The removeable RAM package of claim 2 wherein said sensing means comprises:
   at least three terminals on each of said mating edge connectors which form at least three interconnected terminal pairs when said edge connectors are properly mated together, at least two of said terminal pairs being positioned substantially at opposite ends of said elongated edge connectors;
   at least one jumper line on said RAM package edge connector disposed to coupled first and second ones of said terminal pairs together when said edge connectors are properly mated together, said interlock line in said external device connected to said first terminal pair;
   at least one jumper line on said external device edge connector disposed to couple said second one and a third one of said terminal pairs together when said edge connectors are properly mated together, said third terminal pair connected over a RAM package interlock line to said write preventing means, whereby said sensed voltage level on said external device interlock line appears on said RAM package interlock line only when said at least three terminals of said edge connectors are securely interconnected.

5. The removable RAM package of claim 4 wherein said write preventing means comprises a one-shot multivibrator coupled between said RAM package interlock line and said RAM.

6. The removable RAM package of claim 5 wherein said write preventing means further comprises logic means coupled between the output of said multivibrator and said edge connector for providing a ready signal to said external device to indicate that the removable RAM package is ready to accept writes to said RAM after said sensed voltage level from said external device has been stable for said predetermined time.

7. The removable RAM package of claim 1 which further comprises a programmable real time timer connected on said data bus and said address bus, and coupled to said RAM package edge connector, said timer for storing timing parameters relative to operation of said RAM package, and wherein said interlock circuit comprises:
   means for sensing the level of a voltage on an interlock line in said external device; and
   means for preventing writes to said real time timer until said sensed external voltage level from said external device comprises said predetermined state and has been stable for a predetermined time period.

8. The removable RAM package of claim 7 wherein said sensing means comprises:
   at least three terminals on each of said mating edge connectors which form at least three interconnected terminal pairs when said edge connectors are properly mated together, at least two of said terminal pairs being positioned substantially at opposite ends of said elongated edge connectors;

at least one jumper line on said RAM package edge connector disposed to coupled first and second ones of said terminal pairs together when said edge connectors are properly mated together, said interlock line in said external device connected to said first terminal pair;

at least one jumper line on said external device edge connector disposed to couple said second one and a third one of said terminal pairs together when said edge connectors are properly mated together, said third terminal pair connected over a RAM package interlock line to said write preventing means, whereby said sensed voltage level on said external device interlock line appears on said RAM package interlock line only when said at least three terminals of said edge connectors are securely interconnected.

9. The removable RAM package of claim 8 wherein said write preventing means comprises a one-shot multivibrator coupled between said RAM package interlock line and said real time-timer.

10. The removable RAM package of claim 9 wherein said write preventing means further comprises logic means coupled between the ouput of said multivibrator and said edge connector for providing a ready signal to said external device to indicate that the RAM package is ready to accept writes to said real time timer.

* * * * *